United States Patent [19]

Dent et al.

[11] 4,349,533

[45] Sep. 14, 1982

[54] TOOTHPASTE CONTAINING PH-ADJUSTED ZEOLITE

[75] Inventors: Anthony L. Dent, Bala Cynwyd, Pa.; Elliot P. Hertzenberg, Wilmington, Del.; Howard S. Sherry, Cherry Hill, N.J.

[73] Assignee: PQ Corporation, Valley Forge, Pa.

[21] Appl. No.: 217,602

[22] Filed: Dec. 18, 1980

Related U.S. Application Data

[63] Continuation-in-part of Ser. No. 68,129, Aug. 20, 1979, abandoned.

[51] Int. Cl.$^3$ .................. A61K 7/16; A61K 7/18; A61K 7/28
[52] U.S. Cl. ................................ 424/52; 424/49; 424/50
[58] Field of Search .................... 424/49–58

[56] References Cited

U.S. PATENT DOCUMENTS

| | | | |
|---|---|---|---|
| 3,250,680 | 5/1966 | Menkart et al. | 424/49 |
| 4,132,771 | 1/1979 | Schreiber et al. | 424/52 |
| 4,159,316 | 6/1979 | Januszewski et al. | 424/49 |
| 4,187,287 | 2/1980 | Schreiber et al. | 424/49 |
| 4,193,987 | 3/1980 | Harth et al. | 424/49 |
| 4,209,504 | 6/1980 | Harth et al. | 424/49 |

FOREIGN PATENT DOCUMENTS

| | | | |
|---|---|---|---|
| 378010 | 5/1922 | Fed. Rep. of Germany | 424/49 |
| 55-24112 | 2/1980 | Japan. | |
| 332142 | 7/1930 | United Kingdom. | |

OTHER PUBLICATIONS

Kato et al., Reports of the Institute for Medical and Dental Engineering I, 85: (1973).

Chemical Abstracts 93 #53811s, Aug. 11, 1980, of Jpn. Kokai Tokkyo Koho 80 24,112 Feb. 21, 1980, (Toyo Soda Mfg. Co., Ltd.), "Dentifrices Containing Zeolites".

Chemical Abstracts 75 #91249a (1971) of Kato et al., "Zeolite as Polishing Agent for Dentifrice II, Abrasive Action and Active Fluoride Ion in Zeolite Containing Fluoride".

Chemical Abstracts 73 #101946a (1970) of Kato et al., "Zeolite as Polishing Agent for Dentifrice I, Chemical Properties of Zeolite".

*Primary Examiner*—Shep K. Rose
*Attorney, Agent, or Firm*—Ernest G. Posner; J. Stephen Bobb; Fred Philpitt

[57] ABSTRACT

Crystalline alumino-silicates (zeolites) are multifunctional in dentifrice compositions thereby reducing the number of components required in such formulations. The pH-adjusted zeolites can keep the pH of the dentifrice in the range where caries formation is impossible. The pH-adjusted synthetic or natural zeolites can be prepared or obtained in a particle size range that provides both abrasive cleansing and polishing or lustering of the teeth. The fine particle size and water absorbing capabilities of the zeolite can also provide thickening. Such multifunctional performance allows considerable simplification in the formulation of dentrifice compositions.

5 Claims, No Drawings

TOOTHPASTE CONTAINING PH-ADJUSTED ZEOLITE

This application is a continuation in part of our co-pending U.S. patent application Ser. No. 068,129, filed Aug. 20, 1979, now abandoned.

BACKGROUND OF THE INVENTION

This invention relates to improved dentifrice formulations. In particular, it involves the use of pH-modified synthetic and/or natural zeolites as multifunctional components for dentifrices.

In the United States alone, estimates place the cost of repairing the effects of tooth decay at six billion dollars annually. The first line of defense is the individual's own dental hygiene program. For each person, this primarily involves daily use of a dentifrice to clean the teeth. Modern dental research has shown that decay results from localized demineralization of tooth enamel. This demineralization is caused by the action of acids which are formed by specific bacteria metabolizing fermentable carbohydrates. These bacteria are found adhering to the plaque which forms on the teeth, often comprising as much as 70% of the plaque itself. Further studies have shown that demineralization takes place at a pH of 5.5 or less. Above pH 6 demineralization ceases. (H. J. Sanders; *Chemical and Engineering News*, Feb. 25, 1980.)

Therefore, a proper dentifrice formulation used to clean the teeth, sweeten breath, and reduce tooth decay must do the following:

a. Keep the pH at 6 or above—the non-demineralization zone; and b. Remove the plaque which serves as a situs for the specific bacteria whose metabolic action is the prime cause of tooth decay.

Additionally, since the dentifrice is for human use, it must be biologically compatible and safe for repeated use.

Besides the above objective criteria, dentifrices must be esthetically acceptable to the persons who will use them. Taste and texture must be pleasing and the dentifrice must not produce any unpleasant sensory perceptions. Organoleptic testing has shown that despite objective usefulness of a dentifrice, it will be rejected if its psycho-sensory effects are objectionable.

Modern dentifrice compositions contain numerous components that have various therapeutic and cosmetic functions. Most of these compositions contain some sort of abrasive cleansing agent which aids in the removal of adherent deposits on the teeth. Particulate matter of specific hardness and certain particle size, shape and structure is utilized as such abrasives. These particles must also be compatible with other toothpaste ingredients and safe for repeated human use. Abrasives that are described in the patent literature and have found commercial application include silica xerogels, hydrated silicas, hydrated aluminas, calcium carbonate, dicalcium phosphate (anhydrous and dihydrate), calcium pyrophosphate and insoluble sodium metaphosphate. These agents are usually 2 to 30 $\mu$m in size. Products of about 10 $\mu$m appear to find the most commercial acceptance. Insoluble crystalline materials such as quartz have been found too abrasive for safe use on human dentition.

Many dentifrice formulations contain a polishing or lustering agent in addition to the abrasive. These materials are generally softer and of smaller particle size than the abrasives. These agents are not useful in removing adherent stains and other material from the teeth; instead, they provide so-called luster to the teeth by a fine polishing action. Some of the agents used in this capacity include diatomaceous earth, pyrogenic and aerogel silicas and amorphous alumino-silicates. U.S. Pat. Nos. 3,911,104 and 4,036,949 disclose the use of amorphous alumino-silicates for such polishing agents. These materials have very high silica-to-alumina ratios and are not considered abrasives.

A desirable ingredient for dentifrices is one that provides both abrasive and polishing actions. Such a dual-purpose material greatly simplifies the formulation and production of these multi-component products. Most abrasive particles must be ~10 $\mu$m or more in size to provide adequate action while particles of less than about 1 $\mu$m are required for polishing action. Producing particulate products with such bi-modal or wide range particle size distribution is difficult, expensive and is not done. Some silicas suggested as abrasives are crushed during use to provide particles of the correct size for polishing. The materials that provide sufficient crushed particles for good polishing often exhibit poor abrasion.

Additional siliceous or similar materials are required to thicken toothpastes as well as provide carriers for many additional ingredients.

Zeolites have been suggested as components in toothpastes and powders. Frank (German Empire Patentschrift 378010) suggested the use of what he called the base exchanging property of zeolites to aid in the dissolution of scale. He pointed out that a toothpaste using fine zeolitic powder had a pronounced effect on scale. Menkart and Ricciuti suggested (U.S. Pat. No. 3,250,680) the use of anhydrous zeolites in cosmetic preparations to produce a pleasant warm sensation on hydration during use. Their purpose was an esthetic satisfaction, rather than an objective use. Harth and Becker (U.S. Pat. No. 4,209,504) suggest the use of zeolites as a polishing agent in toothpaste. The main thrust of their invention is the use of zeolite as an agent with no corrosive effect on unlacquered aluminum surfaces. None of these inventions suggested the use of zeolite as an aid in control of dental caries.

Kato et al. (K. Kato, M. Shiba, Y. Okamoto, N. Nagata; *Reports of the Institute for Medical and Dental Engineering* I, 85: 1973) pointed out the compatibility of zeolites with fluoride ion, which is used as a caries preventive.

None of the above suggestions or inventions point to the use of zeolite, natural or synthetic, as a caries preventive in itself, or allude to the possibility of modifying the zeolite so that it can serve in this function. In addition, there are no commercially available dentifrices which contain zeolite (45 FR 20666-20691).

Most commercially available dentifrices have pH's below the demineralization thresold. For example, the following table gives pH values for the commonly used abrasives in stannous fluoride dentifrices (45 FR 20681).

TABLE I

| | Hydrogen Ion Concentration (pH) | |
|---|---|---|
| Abrasive | Test Value | Maximum Test Dilution (w/w) |
| Insoluble sodium metaphosphate | 4.2–5.4 | 1:10 |
| Silica | 4.6–5.1 | 1:10 |

TABLE I-continued

| | Hydrogen Ion Concentration (pH) | |
|---|---|---|
| Abrasive | Test Value | Maximum Test Dilution (w/w) |
| Calcium pyrophosphate | 4.4–5.1 | 1:10 |

The above pH's are well within the range at which demineralization occurs. It would be advantageous to have a formulation outside of the demineralization range which is still acceptable psychosensorily to the persons who will use it.

It is the prime objective of this invention to have the component zeolite impart a pH of 6 or above to the formulation, but below the pH level at which there is personal objection to the taste and sense of dehydration in the mouth. Also, there is no offensive texture. It is an additional object of this invention, simultaneously with provision for aiding in caries control, to provide zeolites, natural and/or synthetic, as a multifunctional component in dentifrices, providing as well polishing and lustering action and abrasion of plaque, thereby simplifying formulation and manufacture of such compositions.

SUMMARY OF THE INVENTION

We have found that crystallized metal alumino-silicates (zeolites) provide an array of functions when compounded into a dentifrice. Natural or synthetic zeolites of the correct particle size range function as abrasives and polishing agents. Surprisingly, this dual functionality does not require a very wide particle distribution since the zeolites provide excellent abrasive action at particle sizes that are about an order of magnitude smaller than comparable prior art materials. Zeolites of such small size contribute the thickening action required for toothpaste. Therapeutic cations such as calcium, indium and stannous ions can be exchanged into the zeolite and added as an integral part of the abrasive.

Most surprisingly, we have found that zeolites can be acid-modified without appreciably destroying their crystalline structure. Authorities in the field state that strong acid will decompose zeolites (D. W. Breck; *Zeolite Molecular Sieves;* John Wiley and Sons; New York: 1974, p. 502 cf.) with either the formation of gel or with separation of insoluble silica without formation of gel. The specific result depends on the initial Al/Si in the starting zeolite. Only mordenite and clinoptilolite have been successfully treated with acid. Normally pH's of slurried zeolites are in the alkaline range; for example, a 10% slurry of Zeolite NaA has a pH of 10–10.5. Our organoleptic studies indicate that pH-unmodified zeolites are unacceptable as a dentifrice component. The high pH produces sensory perceptions which are distasteful to the user and lead to rejection of the dentifrice. Our pH-modified zeolites would obviate such results and would result in a personal acceptance.

A pH-modified zeolite can contribute to the maintenance of the proper pH in the oral environment, which will inhibit the formation of caries. In addition, zeolites can function as abrasives, lustering agents, thickeners, and carriers of ionic and non-ionic components.

This unusual and unexpected combination of capabilities has never been available to dentifrice formulators. Such use of zeolites allows new combinations to be formulated as well as simplifying their preparation to a degree not previously possible.

THE INVENTION

Our multifunctional components for dentifrice compositions comprise various crystalline metallo aluminosilicates or mixtures thereof. These materials are also known as zeolites, and both natural and synthetic zeolites can be employed as our unique dentifrice component. We usually use synthetic zeolites since they are readily available and of consistent properties. U.S. Pat. Nos. 2,882,243–4; 3,012,853; 3,130,007 and 3,329,628 among many others describe zeolites that are suitable as well as methods for preparing them. While most zeolites can be employed according to our invention we usually use zeolites that conform to the following formula:

$$M_{x/n}[(AlO_2)_x(SiO_2)_y]ZH_2O$$

In this formula x and y are integers; the mole ratio of x to y is in the range of 0.001 to 2.0 and Z is an integer from about 1 to 250. M is a metal and n is the valance of said metal.

We often use the various metal forms of Zeolite A which conform to the formula:

$$M_{12/n}[(AlO_2)_{12}(SiO_2)_{12}]ZH_2O$$

We also use the various metal forms of the less siliceous faugasite type zeolite such as Zeolite X, for example, which has the formula:

$$M_{85/n}[(AlO_2)_{85}(SiO_2)_{107}]ZH_2O$$

The various metal forms of Zeolite Y can be useful. Such synthetic zeolites are most conveniently prepared by the thermal treatment of an alumino-silicate gel which is prepared by mixing aqueous sources of silica, alumina and alkali. The hydrothermal treatment causes the desired species to crystallize. Conventional filtering, washing, drying and deagglomeration steps complete the preparation.

Synthetic zeolites are usually prepared in the sodium form while natural zeolites are rarely found in the sodium form. However, any desired metal form can be produced by proper ion exchange procedure. The zeolite can be completely or partially exchanged to achieve greater compatibility with other toothpaste ingredients or greater safety for repeated human use. The zeolite can be used as an ion carrier so that said ion can be added with the zeolite. Stannous, indium, calcium and magnesium ions among others can be added in this manner.

Zeolites appear to be unique dentifrice abrasives in that they are effective even though they have a small ultimate particle size. Our zeolites are approximately an order of magnitude smaller than presently commercially acceptable abrasives that exhibit about the same or less abrasion. Since the zeolites are effective at such small sizes they also function as polishing or lustering agents without crushing or fragmentation. The small particle size and liquid absorbing capacity of our zeolite also enable it to thicken or provide good pasting properties when used in toothpastes. A single component that provides these three functionalities greatly simplifies formulation and manufacture of dentifrices.

A unique use of the internal structure of zeolite involves enzymes which have been found to have beneficial effects in toothpastes as described in U.S. Pat. Nos. 4,058,595 and 4,082,841. These patents are hereby incorporated by reference as fully describing the enzymes which are used in combination with our zeolites. The enzymes employed are protase, carbohydrase or lipase. Mixtures of these materials are effective. These compounds require the presence of group IIA or IIB metal ions to enhance performance and provide stability. The incorporation of these materials in our zeolite is carried out as follows. The zeolite is provided in or ion-exchanged into the desired metal form, usually calcium or zinc. Then the zeolite is heated to remove the water from the pores and cages of the zeolite. The enzymes or mixture of enzymes are absorbed into the zeolite and incorporated into the dentifrice. This procedure assures a high enzyme activity on use.

Numerous other ingredients constitute the balance of the composition and provide various therapeutic, cosmetic and conditioning functions. Humectants prevent hardness in the toothpaste and include, among others, glycerol, sorbitol and propylene glycol. Binders are important for obvious reasons and include gum tragacanth, sodium carboxymethylcellulose, methylcellulose, hydroxyethylcellulose, propylene glycol alginate, Indian gum, Irish moss, carrageenan, starch agar agar and the like. Other ingredients include soaps and synthetic detergents, flavoring agents such as sweeteners and oxygen releasers, buffers, preservatives and coloring agents.

The multifunctional nature of zeolites in dentifrice compositions requires the use of a variety of zeolite types and a wide range of use levels in such compositions. The types of zeolites that are useful have been previously discussed.

Usually zeolites of the A and X structures are used. The calcium and sodium forms of these zeolites are most commonly used. Depending on the purpose for including zeolite very little of the zeolite (about 1% or so) may be formulated into the dentifrice. On the other hand a dentifrice powder might contain well over 90% zeolite. In general, we have found about 5 to 80% of a dentifrice can advantageously comprise a zeolite, a mixture of zeolites, an ion-exchanged zeolite, an impregnated zeolite or a mixture of all these types. We prefer to use 10 to 65% of said materials in a formulation. While zeolites with many metal ions are useful we have found that zeolites that have 20 to 100% of the metal sites exchanged with calcium, magnesium, or zinc appear to be the most useful. Zeolites exchanged to between 10 and 50% of the available exchange sites with stannous or indium ions provide useful therapeutic levels in dentifrice compositions.

The following procedure illustrates certain of the steps by which a zeolite can be prepared and utilized as a dentifrice composition. Zeolite NaA was prepared by hydrothermal treatment of an appropriate alumino-silicate gel. The particle size of this material averaged 2.8 $\mu$m. This material was tested as an abrasive and was found to have an RDA (radioactive dentin abrasion) value of 127. This zeolite was converted to Zeolite CaA by ion exchange. The zeolite was slurried in water and formed into a filter cake of about $\frac{3}{8}''$ on a vacuum filter. Then a solution of 0.1 N $CaCl_2$ in water was passed through the filter cake in 20 minutes. Sufficient solution was used to provide sufficient $Ca^{++}$ ions to replace all of the $Na^+$ ions. The result was that 87% of the exchangeable sodium ions were replaced with calcium. This product had an RDA value of 117 while the particle size remained the same. To a vigorously stirred 10% slurry of the zeolite 3 N hydrochloric acid (HCl) is very slowly added until the pH of the solution is in the 5.5–6.0 range. The sodium form before calcium exchange can be pH adjusted by the slow addition of 8 N sulfuric acid ($H_2SO_4$) to a 10% slurry of the zeolite. Other zeolites are treated in a similar manner. Our chemical analysis has shown that for calcium exchanged zeolites this pH modification is accomplished by replacing approximately 2% of the exchangeable cations with $H_3O^+$, whereas, for the sodium forms of the zeolites approximately 10% of the cations must exchange to $H_3O^{30}$. Table II shows some of the properties of typically pH-modified zeolites, while Table III gives the chemical analysis of some typical pH-modified zeolites.

TABLE II

Properties of pH-Modified Zeolites Powders

| | Acid | Final Slurry pH | LOI (%) | Crystal-linity % XRD* | % By Wt. $Na_2O$ | CaO |
|---|---|---|---|---|---|---|
| NaA | $H_3PO_4$ | 8.5 | 19.1 | 101 | — | — |
| (Experimental) | " | 7.0 | 19.8 | 97 | 15.9 | — |
| | " | 6.0 | 23.1 | 83 | 14.7 | — |
| | " | 5.0 | 20.7 | 5 | 8.4 | — |
| | " | 4.0 | 24.3 | 12 | 6.6 | — |
| | HCl | 7.0 | 21.1 | 97 | — | — |
| | None | 10.7 | 20.8 | 100 | 17.6 | — |
| NaA | None | 11.0 | 20.4 | 94 | 18.2 | — |
| (Commericial) | $H_2SO_4$ | 6.0 | 16.1 | 90 | 15.6 | — |
| NaX | $H_3PO_4$ | 5.0 | 26.8 | 71 | — | — |
| (Experimental) | " | 4.0 | 26.8 | 29 | — | — |
| | None | 10.8 | 22.5 | 98 | — | — |
| NaX | None | 10.2 | 22.8 | 103 | 15.3 | — |
| (Commercial) | $H_2SO_4$ | 5.5 | 25.1 | 108 | 12.6 | — |
| CaA | $H_3PO_4$ | 7.0 | 18.4 | 100 | 0.78 | 17.5 |
| (Experimental) | " | 6.0 | 19.8 | 100 | 0.64 | 15.1 |
| | " | 5.0 | 20.7 | 93 | 0.49 | 14.4 |
| | " | 4.0 | 21.8 | 96 | 0.25 | 13.9 |
| | None | 9.2 | 24.6 | 100* | 0.78 | 14.4 |

*Crystallinity measured against well characterized standards.

TABLE III

| Key Property | Chemical Analyses of pH-Modified Zeolites[a,b] | | | | | |
|---|---|---|---|---|---|---|
| | NaHA | CaHA | | NaHX | | CaHx |
| $SiO_2$ (wt %) | 33.2 | 32.0 | 33.4 | 37.1 | 37.2 | 35.7 |
| $Al_2O_3$ (wt %)[c] | 28.9 | 29.6 | 30.2 | 26.2 | 26.7[d] | 25.3 |
| $Na_2O$ (wt %) | 16.0 | 2.2 | 4.5 | 13.1 | 9.1 | 5.4 |
| CaO (wt %) | — | 13.8 | 11.5 | — | — | 8.2 |
| $H_2O$ (wt % by LOI) | 21.9 | 22.4 | 20.4 | 23.6 | 27.0 | 25.4 |
| Totals | 100.0 | 100.0 | 100.0 | 100.0 | 100.0 | 100.0 |
| Si/Al Atom Ratio | 0.97 | 0.92 | 0.94 | 1.20 | 1.18 | 1.20 |
| Slurry pH (5% sol. in D°.I. $H_2O$/in .1N NaCl sol) | 6.8/— | 9.2/7.3 | 8.4/7.5 | — | 7.0/6.0 | 6.3/6.0 |
| Meq $Na^+$ (anhydrous) | 6.61 | 0.92 | 1.82 | 5.53 | 4.02 | 2.34 |
| Meq $Ca^{++}$ (anhydrous)[e] | — | 6.34 | 5.15 | — | — | 3.92 |
| Meq $H_2O$ (anhydrous) | 0.77 | 0.12 | 0.41 | 0.86 | 2.37 | 0.14 |

TABLE III-continued

Chemical Analyses of pH-Modified Zeolites[a,b]

| Key Property | | NaHA | CaHA | NaHX | CaHx |
|---|---|---|---|---|---|
| % Exchg $\left( \dfrac{\text{Meq } H_3O^+ \cdot 100}{\text{Meq } [H_3O^+ + Ca^{++}]} \right)$ | 10/10 | 2/88 | 6/75 | 13/13 | 37/37 | 2/63 |

[a]Commerical NaA used as starting material.
[b]Commerical NaX used as starting material.
[c]Determined by difference.
[d]Determined by analytical methods.
[e]Determined by difference; total sodium as reported in Table II.

In order to check the integrity of the crystalline structure, four zeolite powders that had been pH-modified in the manner described above were subjected to re-exchange. In each case 25 grams of the zeolite powder was dispersed in 200 ml of deionized water, and the slurry was adjusted to a pH of ~11 using ~5% NaOH. After filtering, the materials were washed with deionized water and air-dried. For the calcium-exchanged samples, an additional step involving washing the filter cakes with a 500 ml solution of 10% $CaCl_2 \cdot 2H_2O$ was included. The crystallinity was measured by X-ray diffraction (XRD) is reported in Table IV. These results indicate that no significant reduction in crystallinity occurred during the preparation of these samples. Further evidence to support the premise that no structural changes occurred in these products is provided by comparing the constant values of the Si/Al atom ratios in Tables 2 and 3. More severe treatment, e.g., at pH 4, would cause extensive structural damage, especially to Zeolite A.

TABLE IV

Crystallinity of pH-Modified Zeolites[a]

| Crystallinity (% XRD)[b] | Na—A | CaA | Na—X | CaX |
|---|---|---|---|---|
| Initial Material | 94 | —[a] | 103 | —[a] |
| After pH Modification | 90 | 81 | 108 | 109 |
| After pH Modification and Back-Exchange[c] | 94 | 89 | 109 | 109 |
| Lowest Slurry pH During Modification | 5.9 | 5.9 | 5.4 | 5.4 |

[a]Commercial Na—A and commercial NaX zeolites were used as the starting materials, respectively, for these samples.
[b]Moisture contents (LOI) of all samples are in the range that does not affect XRD measurements.
[c]Back-exchange procedure described in text.

The pH-modified zeolites are compatible with fluoride ion supplying chemicals used in dentifrice formulations. In the following discussions, MHZ represents a zeolite with cation M and pH modification, for example, NaHA, sodium A zeolite which has been pH-modified as described above.

The abrasive properties of zeolites are realized at very small average particle sizes. While most prior art abrasives are required in particle sizes up to 30 $\mu$m to realize their abrasive nature, the abrasive nature of zeolite is apparent in materials of particle sizes of 10 $\mu$m or less. We prefer zeolites of 5 $\mu$m or less with a lower limit of about 0.5 $\mu$m. A most preferred range is 0.5 to 3.5 for zeolites such as Zeolite NaHA, Zeolite CaHA, Zeolite NaHX and Zeolite CaHX. Some examples of zeolites and their abrasive action are summarized in the following table; calcium pyrophosphate is the standard, and the value therefor is 100.

TABLE V

Radioactive Dentin Abrasion Values for Zeolites and Prior Art Materials

| Abrasive Agent | Average Particle Size ($\mu$m) | RDA Value |
|---|---|---|
| Calcium Pyrophosphate | — | 100 |
| Prior Art Silica Xerogel | 8.0 | 117 |
| Experimental Zeolite NaHA | 2.8 | 127 |
| Experimental Zeolite NaHA | 4.6 | 166 |
| Experimental Zeolite CaHA | 2.8 | 117 |
| Commercial Zeolite NaA | 6.6 | 166 |
| Commercial Zeolite NaA | 4.2 | 174 |
| Commercial Zeolite NaA | 3.0 | 110 |
| Experimental Zeolite NaHX | 3.4 | 154 |

These results indicate that pH-modified zeolites of relatively small particle size are very effective abrasives.

Toothpaste compositions that are formulated with zeolites and can accommodate water in the composition have the following compositions.

| | General | Preferred |
|---|---|---|
| Zeolite (% by weight) | 5–80 | 10–65 |
| Humectant (% by weight) | 10–75 | 15–55 |
| Water (% by weight) | 10–50 | 15–45 |
| Sodium Lauryl Sulfate/Glycerin* | 3–10 | 3–10 |
| Binder | 2–5 | 2–5 |

*Mixture consists of 79% Sodium Lauryl Sulfate and 21% glycerin.

The balance of the composition to 100% consists of optional and cosmetic ingredients such as sweeteners, oxygen release agents, buffers, preservatives and coloring and flavoring agents.

Toothpastes which contain a fluoride or enzyme source should be formulated with the following composition.

| | General | Preferred |
|---|---|---|
| Zeolite (% by weight) | 5–80 | 10–65 |
| Humectant | 10–90 | 15–75 |
| Sodium Lauryl Sulfate/Glycerin* | 3–15 | 3–15 |
| Binder | 2–7 | 2–7 |
| Flavorant and Colorant | 0.5–4 | 0.5–2 |
| Fluoride or Enzyme Source | 0.05–0.75 | .2–.75 |

*Mixture consists of 79% Sodium Lauryl Sulfate and 21% glycerin.

The balance of the composition consists of optional and cosmetic ingredients such as sweeteners, oxygen release agents, buffers, preservatives and coloring agents. Water not associated with the other ingredients is not added to this composition.

EXAMPLES

The following examples illustrate certain embodiments of our invention but do not indicate the scope of our invention which is fully described in the specification and claims. All proportions are in parts by weight (pbw) or weight percent (%) unless otherwise specified.

Example 1

A toothpaste composition using zeolite as an abrasive/polishing agent having the following composition was prepared.

| | |
|---|---|
| Zeolite NaHA (2.8 μm average particle size) | 44.0 pbw |
| Sorbitol Syrup (70% in water) | 35.0 pbw |
| NaCMC | 0.3 pbw |
| Stannous Fluoride | 0.4 pbw |
| 21% Sodium Lauryl Sulfate/79% Glycerin | 12.0 pbw |
| Saccharin | 0.2 pbw |
| Coloring Agents | 0.2 pbw |
| Flavorants | 0.2 pbw |
| Water | To 100 pbw |

This composition showed completely satisfactory abrasion and cleansing effects, and was personally acceptable.

Example 2

The Zeolite NaA described was ion-exchanged using a solution of $CaCl_2$ to provide Zeolite CaA wherein 93% of the available sodium was replaced by calcium. This material was pH-modified and substituted for the Zeolite NaHA in the composition described in Example 1. This composition exhibited satisfactory abrasion and cleansing effects and personal acceptability.

Example 3

The Zeolite CaHA as described in Example 2 was formulated into the following dentifrice.

| | |
|---|---|
| Zeolite CaHA | 41.0 pbw |
| Sorbitol Syrup | 44.0 pbw |
| 21% Sodium Lauryl Sulfate/79% Glycerin | 15.8 pbw |
| Saccharin | 0.2 pbw |
| Colorant | 0.5 pbw |
| Flavorant | 0.2 pbw |
| Stannous Fluoride | 0.03 pbw |
| Water | To 100 pbw |

This composition shows zeolite as an abrasive, lustering agent, thickening agent and a carrier for stannous fluoride. The results are satisfactory.

Example 4

The zeolite of example 2 was formulated as follows:

| | |
|---|---|
| Zeolite CaHA | 41.0 pbw |
| Sorbitol Syrup | 44.0 pbw |
| 21% Sodium Lauryl Sulfate/79% Glycerin | 15.8 pbw |
| Saccharin | 0.2 pbw |
| Colorant | 0.5 pbw |
| Flavorant | 0.2 pbw |
| Sodium Fluoride | 0.02 pbw |
| Water | To 100 pbw |

The results are satisfactory.

Example 5

The zeolite of Example 2 was formulated as follows:

| | |
|---|---|
| Zeolite CaHA | 41.0 pbw |
| Sorbitol Syrup | 44.0 pbw |
| 21% Sodium Lauryl Sulfate/79% Glycerin | 15.8 pbw |
| Saccharin | 0.2 pbw |
| Colorant | 0.2 pbw |
| Flavorant | 0.2 pbw |
| Sodium Monofluorophosphate | 0.04 pbw |
| Water | To 100 pbw |

The results are satisfactory.

Example 6

The NaHA of Example 1 was substituted for CaHA in Examples 3, 4 and 5.

Example 7

Two samples of Zeolite NaHX are prepared with average particle sizes of 2.2 μm and 3.4 μm. Each of these materials is substituted for the Zeolite CaHA in the composition described in Example 3, 4 and 5, with satisfactory results.

Example 8

The sample of Zeolite NaX with a particle size of 2.2 μm is ion-exchanged to the calcium form using $CaCl_2$ solution. Over 90% of exchangeable sites are converted from sodium to calcium. This zeolite is pH-adjusted and substituted for Zeolite CaHA in Examples 3, 4 and 5 with satisfactory results.

Example 9

The Zeolite CaHX described in Example 8 is substituted for ⅓ (22 pbw) of the Zeolite CaHA in the composition described in Example 2. The zeolite composition is 22 pbw of Zeolite CaHX with completely satisfactory results.

We claim:

1. A dentifrice formulation having a pH range outside the 4.2 to 5.4 demineralization threshold and which is acceptable psychosensorily to persons who will use it; said dentifrice being a toothpaste containing 5–80% by weight pH-modified zeolite and being free from zeolites that are not pH-modified;

said pH-modified zeolite being the result of slurrying a zeolite and slowly adding acid solution until the pH of the solution is 5.5–6.0, and therefore personally acceptable, said non-pH-modified zeolites not having personal acceptance;

said pH-modified zeolite having a slurry pH of 5.5–6.0 without the significant reduction of the crystal structure that would be caused by more severe treatment at pH 4 or less;

said pH-modified zeolite having a particle size of 0.5 to 3.5 μm and about an order of magnitude smaller than commercially acceptable abrasive agents that exhibit the same or less abrasion;

said acid slurried pH-modified zeolite not being crushed or fragmented or use but still providing polishing and lustering and providing good pasting properties to said toothpaste, said toothpaste being free from other abrasives and lustering agents;

said acid slurried pH-modified zeolite imparting a pH of 6 or above but below the pH at which there is personal objection to the taste and sense of dehydration to the mouth.

2. The dentifrice of claim 1 wherein 20 to 100% of the available exchange sites are occupied by calcium, magnesium or zinc.

3. The dentifrice of claim 1 wherein the zeolite is synthetic and selected from the group consisting of Zeolite NaHA, Zeolite CaHA, Zeolite ZnHA, Zeolite MgHA, Zeolite NaAX, Zeolite CaHX, Zeolite ZnHX, Zeolite MgHX, and mixtures of said zeolites.

4. The dentifrice of claim 1 wherein the zeolite or mixture of zeolites is ion-exchanged and 10 to 50% of the available exchange sites are occupied with stannous or indium ions.

5. The dentifrice of claim 1 wherein said zeolite has been mixed with up to 600 parts per million of fluorine available from stannous fluoride, sodium fluoride or sodium monofluorophosphate.

* * * * *